United States Patent
Zülli et al.

(10) Patent No.: US 6,843,984 B2
(45) Date of Patent: Jan. 18, 2005

(54) HAIR TREATMENT PRODUCTS

(75) Inventors: Fred Zülli, Küttingen (CH); Ester Belser-Gisi, Aarau (CH); Reto Muggli, Olten (CH); Thomas Karlen, Aarau (CH)

(73) Assignee: Mibelle AG Cosmetics, Buchs (CH)

(*) Notice: Subject to any disclaimer, the term of this patent is extended or adjusted under 35 U.S.C. 154(b) by 133 days.

(21) Appl. No.: 10/027,435

(22) Filed: Dec. 21, 2001

(65) Prior Publication Data
US 2002/0131942 A1 Sep. 19, 2002

(30) Foreign Application Priority Data
Dec. 22, 2000 (CH) ................................. 2520/00

(51) Int. Cl.⁷ .................................................. A61K 7/06
(52) U.S. Cl. ...................................... 424/74; 424/70.1
(58) Field of Search ........................... 424/74, 70.1, 925

(56) References Cited

U.S. PATENT DOCUMENTS 5,962,517 A    10/1999    Murad

FOREIGN PATENT DOCUMENTS

| EP | 0 768 079 A1 | 4/1997 |
|---|---|---|
| EP | 0 955 051 A1 | 11/1999 |
| EP | 0 995 051 A1 | 11/1999 |
| EP | 1 072 253 A1 | 1/2001 |
| EP | 1 072 254 A1 | 1/2001 |
| EP | 1 086 693 A1 | 3/2001 |
| WO | WO 98/33494 | 8/1998 |
| WO | WO 98/42309 | 10/1998 |
| WO | WO 99/36032 | 7/1999 |
| WO | WO 99/66881 | 12/1999 |
| WO | WO 00/28977 | 5/2000 |
| WO | WO 00/72817 A1 | 12/2000 |
| WO | WO 01/06997 * | 2/2001 |

* cited by examiner

*Primary Examiner*—Jyothsna Venkat
(74) *Attorney, Agent, or Firm*—Maginot, Moore & Beck

(57) ABSTRACT

Hair treatment products comprising in an aqueous phase a mixture of (a) water soluble procyanidins and (b) oil soluble free tocopherols, both components having an affinity to the hair, protect the hair against damage on heat drying, against environmental influences and hair treatments, and they protect other components of said hair treatment products against oxidation and degradation.

4 Claims, No Drawings

HAIR TREATMENT PRODUCTS

BACKGROUND OF THE INVENTION

The present invention relates to hair treatment products for protecting hair against damage on heat drying, against environmental influences and hair treatments as well as for protecting other components of said hair treatment products against oxidation and degradation.

Antioxidants are essential substances in nature. They are used in cosmetics for protecting the compounds of said cosmetics and for protecting the skin against oxidative stress.

Oxidative stress is caused by ROS (Reactive Oxygen Species—reactive oxygen molecules). ROS are formed above all in water, since water is always saturated with oxygen.

Frequently, in cosmetics only oil soluble antioxidants are used, since quite a number of suitable substances are available, such as 3-tert.-butyl-4-hydroxyanisole or alpha-tocopherol.

However, the use of water soluble antioxidants is limited, since no suitable substances are available on the market.

Vitamin C (ascorbic acid) is a water soluble antioxidant, which is widespread in nature but is rarely used in cosmetics, since it is very unstable.

Oligomeric procyanidins, isolated from grape seeds or other plant parts, are very good antioxidants, which are useful in cosmetics. Procyanidins are polyphenols on the basis of catechin and epicatechin.

Thus, the publication U.S. Pat. No. 5,648,377 discloses the use of oligomeric procyanidins in combination with carotinoids for combating radicals in foodstuffs, foodstuff complements, cosmetic and pharmaceutical preparations.

However, the use of oligomeric procyanidins is not unproblematic, since said compounds are only conditionally stable if dissolved in water. Therefore, so far the use of such oligomeric procyanidins was essentially limited to dry products such as capsules or tablets as foodstuff complements.

The publication EP-A1-1,086,693 discloses the stabilization of proanthocyanidins in various products, such as tablets, foodstuffs and cosmetics by means of vitamin B6. The disclosed proanthocyanidins are principally dimers, in contrast to the present invention which is mainly directed to the use of oligomers. Furthermore, vitamin B6 is a water soluble vitamin. The use of grape seed extract and vitamin B6 in cosmetics, such as shampoos, in said publication is exclusively made for stabilizing the proanthocyanidins. Protection of hair by combining procyanidins with pure tocopherol cannot be deduced therefrom, just as little as the affinity of such a combination to hair. The example of a hair tonic comprising vitamin E acetate does not give any protection to the hair, since vitamin E acetate does not have sufficient antioxidant activity. However, vitamin E acetate can be cleaved in the skin to form pure tocopherol which then shows certain activities for promoting hair growth.

The publication EP-A1-0,768,079 discloses the use of dimeric proanthocyanidins for promoting hair growth. Whereas the described product additionally comprises free tocopherol, the publication does not disclose nor let deduce affinity of the product to hair, and thus does not disclose any protection of hair against radicals; which is not the purpose of said publication either.

SUMMARY OF THE INVENTION

The present invention is based of the surprising finding that oligomeric procyanidins in an aqueous solution are stabilized by the addition of tocopherols, which are introduced into the aqueous solution by means of cosmetic solubilizers, such as PEG-40 hydrogenated castor oil. On the other hand, stability of the tocopherols is improved by the presence of oligomeric procyanidins.

Thus, e.g., the antioxidant activity of a mixture of 0.5 percent by weight of oligomeric procyanidins and 5 percent by weight of tocopherol remains stable for more than 8 months. Furthermore, this mixture of antioxidants also shows a synergistic effect with respect to the inhibition of UV-A induced formation of toxic substances in squalene.

One object of the present invention is to provide a hair treatment product for protecting hair against damage on heat drying, against environmental influences and hair treatments as well as for protecting other components of said hair treatment product against oxidation and degradation.

Another object of the present invention is to provide such hair treatment product which are based on an aqueous formulation and which are either a "leave on" product, i.e. a product which remains on the hair, or a "rinse off" product, i.e. a product which is washed out.

DETAILED DESCRIPTION OF THE INVENTION

The above and other objects are achieved by a hair treatment product for protecting hair against damage on heat drying, against environmental influences and hair treatments as well as for protecting other components of said hair treatment product against oxidation and degradation, said hair treatment product comprising in an aqueous phase a mixture of (a) water soluble procyanidins and (b) oil soluble free tocopherols, both components having an affinity to hair.

Preferably, the percentage of said water soluble procyanidins (a) is from 0.00005 to 5 percent by weight and the percentage of said oil soluble free tocopherols (b) is from 0.00025 to 10 percent by weight.

Preferably, said water soluble procyanidins (a) are present in oligomeric form, and comprise 10 to 50 subunits.

It is known that hair is damaged by oxidative stress, such as, e.g., by UV irradiation. However, there are hardly any investigations with respect to the damages caused by heat drying of hair, particularly by means of hair dryers.

Surprisingly, it was now found that such hair drying may heavily damage hair, especially in view of the fact that such a treatment is carried out very often.

The damage is mainly caused by the activation of oxygen dissolved in the water film on the wet hair by the heat, that is that ROS (Reactive Oxygen Species—reactive oxygen molecules) may be formed. The ROS, e.g. singlet oxygen or oxygen radicals, then react with the constituents of the hair surface and thus damage the hair structure. Among other reactions, the proteins on the hair surface are oxidized and degraded. Said proteins may then be washed off from hair in the form of amino acids, peptides and proteins.

The following tests show in detail the surprising effects of the combination of active ingredients comprising oligomeric grape seed procyanidins and tocopherols. In particular they show:

Adsorption of tocopherol on the hair surface (Test 1);
Protection of hair against damage on heat drying (Test 2); and
Protection of hair against damage by sea water and UV irradiation (Test 3).

Further active ingredients of the hair treatment product of the present invention protecting hair against oxidation and/ or degradation, particularly photo oxidation, are e.g.: vitamin C and vitamin C derivatives, vitamin A and vitamin A derivatives, perfume oils, unsaturated lipids and proteins.

In following tests and preparations all amounts are given in percents by weight.

Tests

The following tests were carried out with commercially available European hair and the following combination of active ingredients:

| | |
|---|---|
| Ethyl Alcohol | 30.0% |
| Glycerine | 40.0% |
| Polyoxyethylene (40) Hydrogenated Castor Oil | 10.0% |
| Mixed Tocopherols | 5.0% |
| Procyanidins (Grape seed extract) | 0.4% |
| Water | ad 100% |

For the tests this combination of active ingredients was diluted with water to 2.5%, said dilution of active ingredients being hereafter shortly called "dilution".

Test 1 (Adsorption of Tocopherol on the Hair Surface)

2 g of hair were incubated in 20 ml of the dilution with stirring for 10, 20, and 60 minutes, respectively. Thereafter, the hair was rinsed with water and air dried. Then, the hair was extracted with 50 ml isopropanol each. The extracts were then vacuum dried and thereafter dissolved in 1 ml ethanol. The tocopherol content was determined by HPLC analysis.

| Results | |
|---|---|
| Incubation time | Amount of tocopherol on 2 g of hair |
| 10 minutes | 0.1 mg |
| 20 minutes | 0.4 mg |
| 60 minutes | 1.0 mg |

Test 2 (Protection of Hair Against Damage on Heat Drying)

The hair was first washed with a shampoo and rinsed. Then, the hair was incubated for 10 minutes in the dilution. Thereafter it was rinsed with water and dried by means of a hair drier. The dried hair was again sprayed with water and again dried by means of a hair drier. This procedure was repeated 4 and 9 times, respectively. The hair was then extracted with a 2% aqueous sodium dodecylsulfate solution. The extract was then filtered. The protein and peptide content of the extract was then determined by means of the method of Bradford. In the control the hair was treated the same way, except that the hair was incubated in water instead of in the dilution

| Results: Amount of protein in the extract | |
|---|---|
| After heat drying for 5 times | |
| Control | 30 µg/ml |
| Test with dilution | 7 µg/ml |

| -continued | |
|---|---|
| Results: Amount of protein in the extract | |
| After heat drying for 10 times | |
| Control | 47 µg/ml |
| Test with dilution | 19 µg/ml |

Test 3 (Protection of Hair Against Damage by Sea Water and UV Irradiation)

The hair was first washed with a shampoo and rinsed. Then, the hair was incubated for 60 minutes in the dilution. Thereafter it was rinsed with water and air dried. The dried hair was then irradiated with UV light (control: without UV irradiation). The hair was then extracted with a 2% aqueous sodium dodecylsulfate solution or with sea water. The extract was then filtered. The protein and peptide content of the extract was then determined by means of the method of Bradford. In the control the hair was treated the same way, except that the hair was incubated in water instead of in the dilution.

| Results: Amount of protein in the various extracts | |
|---|---|
| Sodium Dodecyl Sulfate extract | |
| Without UV, without dilution treatment | 36 µg/ml |
| Without UV, with dilution treatment | 10 µg/ml |
| With UV, without dilution treatment | 50 µg/ml |
| With UV, with dilution treatment | 12 µg/ml |
| Sea water extract | |
| Without UV, without dilution treatment | 16 µg/ml |
| Without UV, with dilution treatment | 10 µg/ml |
| With UV, without dilution treatment | 28 µg/ml |
| With UV, with dilution treatment | 16 µg/ml |

Preparations

A. Hair shampoo with grape seed procyanidins and tocopherol

| | |
|---|---|
| Sodium Dodecyl Sulfate. 70% | 12.00% |
| Cocyl Amide Propylbetaine. 35% | 7.00% |
| Perfume | 0.50% |
| Glycerin | 0.02% |
| Ethyl Alcohol | 0.02% |
| Polyoxyethylene (40) Hydrogenated Castor Oil | 0.01% |
| Preservative | 0.1–1.0% |
| Mixed Tocopherols | 0.005% |
| Procyanidins (Grape seed extract) | 0.0005% |
| Water | ad 100% |

B. Hair conditioner with grape seed procyanidins and tocopherol

| | |
|---|---|
| Cetyl Aryl Alcohol | 4.50% |
| Hexadecyltrimethylammonium Chloride | 2.50% |
| Dimethylsiloxane-Glycol Copolymer | 5.00% |
| Perfume | 0.50% |
| Citric Acid | for pH 3.5 |
| Glycerine | 2.0% |
| Ethyl Alcohol | 1.0% |
| Polyoxyethylene (40) Hydrogenated Castor Oil | 0.5% |
| Mixed Tocopherols | 0.25% |
| Procyanidins (Grape seed extract) | 0.10% |
| Preservative | 0.1–1.0% |
| Water | ad 100% |

Preparations

C. Hair tip fluid with grape seed procyanidins and tocopherol

| | |
|---|---|
| Dimethylpolysiloxane | 25.00% |
| Methylcyclopolysiloxane | 71.00% |
| Dimethylsiloxane-Glycol Copolymer | 2.00% |
| Perfume | 1.00% |
| Glycerine | 0.2% |
| Ethyl Alcohol | 0.4% |
| Polyoxyethylene (40) Hydrogenated Castor Oil | 0.4% |
| Mixed Tocopherols | 0.05% |
| Preservative | 0.1–1.0% |
| Procyanidins (Grape seed extract) | 0.05% |

D. Hair spray aerosol with grape seed procyanidins and tocopherol

| | |
|---|---|
| Acrylic/Acrylate Copolymer | 3.00% |
| 2-Amino-2-Methyl-1-Propanol | 0.70% |
| Water | 20.00% |
| Glycerine | 0.02% |
| Polyoxyethylene (40) Hydrogenated Castor Oil | 0.02% |
| Mixed Tocopherols | 0.001% |
| Procyanidins (Grape seed extract) | 0.0005% |
| Methoxymethane | 40.00% |
| Water | ad 100% |

E. Styling gel with grape seed procyanidins and tocopherol

| | |
|---|---|
| Carboxyvinylpolymer | 1.00% |
| Sodium Hydroxide solution. 30% | 1.10% |
| PVP/VA Copolymer | 4.00% |
| Glycerine | 5.00% |
| Ethyl Alcohol | 2.0% |
| Polyoxyethylene (40) Hydrogenated Castor Oil | 1.0% |
| Tocopherol | 0.5% |
| Procyanidins (Grape seed extract) | 0.1% |
| Preservative | 0.1–1.0% |
| Water | ad 100% |

F. Conditioner with grape seed procyanidins. tocopherol and retinyl palpitate

| | |
|---|---|
| Cetyl/Stearyl Alcohol | 4.50% |
| Hexadecyltrimethylammonium Chloride | 2.50% |
| Dimethylsiloxane-Glycol Copolymer | 5.00% |
| Perfume | 0.50% |
| Citric Acid | for pH 3.5 |
| Polyoxyethylene (40) Ethyl/Stearyl Ether | 1.00% |
| Glycerin | 2.0% |
| Ethyl Alcohol | 2.0% |
| Polyoxyethylene (40) Hydrogenated Castor Oil | 1.0% |
| Mixed Tocopherols | 0.001% |
| Procyanidins (Grape seed extract) | 0.5% |
| Vitamin A Palmitate | 1.00% |
| Preservative | 0.1–1.0% |
| Water | ad 100% |

G. Hair tonic with grape seed procyanidins. tocopherol and borage oil

| | |
|---|---|
| Ethyl Alcohol | 30.00% |
| Borage Seed Oil | 2.5% |
| Polyoxyethylene (60) Hydrogenated Castor Oil | 1.00% |
| Polyoxyethylene (40) Hydrogenated Castor Oil | 1.00% |
| Perfume | 0.50% |
| Mixed Tocopherols | 0.25% |
| Procyanidins (Grape seed extract) | 0.25% |
| Preservative | 0.1–1.0% |
| Water | ad 100% |

H. Hair water for treating the scalp with grape seed procyanidins and tocopherol

| | |
|---|---|
| Polyoxyethylene (20) Sorbitan Monolaurate | 2.0% |
| Perfume | 0.5% |
| Glycerine | 3.0% |
| D-Sorbitol | 8.0% |
| Ethyl Alcohol | 2.0% |
| Polyoxyethylene (40) Hydrogenated Castor Oil | 2.00% |
| Mixed Tocopherols | 1.0% |
| Procyanidins (Grape seed extract) | 0.1% |
| Preservative | 0.1–1.0% |
| Water | ad 100% |

I. Non-aerosol hair spray with grape seed procyanidins and tocopherol

| | |
|---|---|
| Acrylic/Acrylate Copolymer | 3.00% |
| 2-Amino-2-Methyl-1-Propanol | 0.70% |
| Ethyl Alcohol | 10.00% |
| Glycerine | 0.6% |
| Polyoxyethylene (40) Hydrogenated Castor Oil | 0.3% |
| Mixed Tocopherols | 0.1% |
| Procyanidins (Grape seed extract) | 0.2% |
| Preservative | 0.1–1.0% |
| Water | ad 100% |

What is claimed is:

1. A hair treatment product for protecting hair against damage on heat drying, against environmental influences and hair treatments as well as for protecting other components of said hair treatment product against oxidation and degradation, said hair treatment product comprising an aqueous phase of a mixture of (a) water soluble procyanidins and (b) oil soluble free tocopherols, in an effective amount for adsorption of the tocopherols on the hair surface.

2. A hair treatment product as set forth in claim 1 wherein the percentage of said water soluble procyanidins (a) is from 0.00005 to 5 percent by weight and the percentage of said oil soluble free tocopherols (b) 0.00025 to 10 percent by weight.

3. A hair treatment product as set forth in claim 1 wherein said water soluble procyanidins (a) are present in an oligomeric form.

4. A hair treatment product as set forth in claim 3 wherein said water soluble procyanidins (a) comprise 10 to 50 subunits.

* * * * *